United States Patent
Doerr

(10) Patent No.: US 9,462,962 B2
(45) Date of Patent: Oct. 11, 2016

(54) IMPLANT AND APPLICATOR

(75) Inventor: Thomas Doerr, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 1023 days.

(21) Appl. No.: 13/070,401

(22) Filed: Mar. 23, 2011

(65) Prior Publication Data

US 2011/0251516 A1 Oct. 13, 2011

Related U.S. Application Data

(60) Provisional application No. 61/323,361, filed on Apr. 13, 2010.

(51) Int. Cl.
| | | |
|---|---|---|
| *A61M 5/44* | (2006.01) | |
| *A61B 10/02* | (2006.01) | |
| *A61F 7/12* | (2006.01) | |
| *A61M 37/00* | (2006.01) | |
| *A61B 5/07* | (2006.01) | |
| *A61B 17/00* | (2006.01) | |
| *A61K 9/50* | (2006.01) | |
| *A61B 5/00* | (2006.01) | |
| *A61F 7/00* | (2006.01) | |
| *A61K 9/00* | (2006.01) | |
| *A61N 1/40* | (2006.01) | |
| *A61N 7/02* | (2006.01) | |

(52) U.S. Cl.
CPC . *A61B 5/07* (2013.01); *A61F 7/12* (2013.01); *A61B 5/4839* (2013.01); *A61B 5/6847* (2013.01); *A61B 5/6882* (2013.01); *A61B 2017/00504* (2013.01); *A61B 2560/0219* (2013.01); *A61F 2007/0071* (2013.01); *A61F 2007/126* (2013.01); *A61K 9/0009* (2013.01); *A61K 9/0024* (2013.01); *A61K 9/5094* (2013.01); *A61N 1/406* (2013.01); *A61N 7/02* (2013.01)

(58) Field of Classification Search
None
See application file for complete search history.

(56) References Cited

U.S. PATENT DOCUMENTS

| | | | |
|---|---|---|---|
| 3,653,385 A | | 4/1972 | Burton |
| 3,731,681 A | * | 5/1973 | Blackshear et al. .......... 604/141 |
| 5,411,508 A | * | 5/1995 | Bessler et al. ................. 606/153 |
| 5,843,028 A | * | 12/1998 | Weaver et al. ................ 604/514 |
| 6,632,216 B2 | * | 10/2003 | Houzego et al. ........... 604/890.1 |
| 6,689,125 B1 | * | 2/2004 | Keith et al. ..................... 606/32 |
| 7,346,391 B1 | | 3/2008 | Osorio |
| 2003/0167000 A1 | | 9/2003 | Mullick |
| 2005/0222537 A1 | | 10/2005 | Dinsmoor |

(Continued)

FOREIGN PATENT DOCUMENTS

| | | |
|---|---|---|
| EP | 0543498 | 5/1993 |
| EP | 1952825 | 8/2008 |

OTHER PUBLICATIONS

European Search Report dated Nov. 3, 2011 (19 pages).

(Continued)

*Primary Examiner* — Devin Henson
*Assistant Examiner* — Matthew Kremer
(74) *Attorney, Agent, or Firm* — Arc IP Law, PC; Joseph J. Mayo

(57) ABSTRACT

Embodiments of the invention include an implant having an energy converter, wherein the converter is designed to convert applied energy to heat. In embodiments of the invention, the energy converter is situated in such a way that heat generated from the energy conversion is active at an outer surface of the implant.

13 Claims, 5 Drawing Sheets

(56) References Cited

U.S. PATENT DOCUMENTS

| | | | |
|---|---|---|---|
| 2005/0278014 A9* | 12/2005 | Daum et al. | 623/1.15 |
| 2006/0025713 A1* | 2/2006 | Rosengart et al. | 604/5.02 |
| 2006/0041182 A1* | 2/2006 | Forbes et al. | 600/12 |
| 2006/0094983 A1* | 5/2006 | Burbank et al. | 600/567 |
| 2006/0129216 A1 | 6/2006 | Hastings | |
| 2006/0167339 A1 | 7/2006 | Gilad | |
| 2006/0253151 A1 | 11/2006 | Nun | |
| 2007/0191816 A1* | 8/2007 | Behan et al. | 604/890.1 |
| 2007/0196281 A1 | 8/2007 | Jin | |
| 2007/0231393 A1* | 10/2007 | Ritter et al. | 424/489 |
| 2007/0239260 A1* | 10/2007 | Palanker et al. | 623/1.15 |
| 2008/0103584 A1* | 5/2008 | Su et al. | 623/1.16 |
| 2008/0243151 A1 | 10/2008 | Binmoeller | |
| 2009/0005656 A1 | 1/2009 | Najafi | |
| 2010/0023000 A1 | 1/2010 | Stevenson | |

OTHER PUBLICATIONS

European Search Report dated Jul. 20, 2011 (6 pages).

* cited by examiner

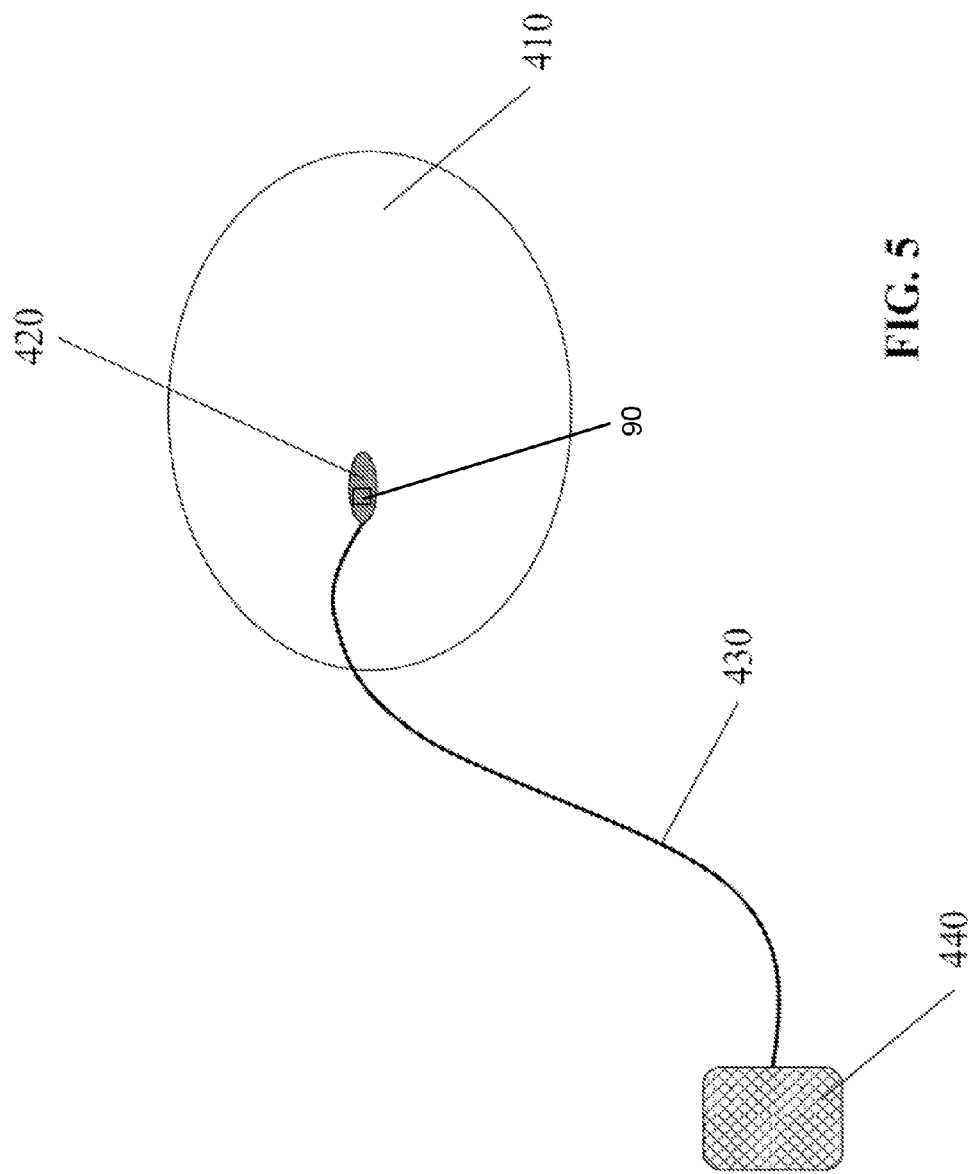

IMPLANT AND APPLICATOR

This application claims the benefit of U.S. Provisional Patent Application 61/323,361, filed 13 Apr. 2010, the specification of which is hereby incorporated herein by reference.

BACKGROUND OF THE INVENTION

1. Field of the Invention

Embodiments of the invention relate to an implant having an energy converter, in particular a microimplant for local delivery of a medication or the like.

2. Description of the Related Art

A fundamental problem of such implants is fixing the implants at a given location in a body.

Many types of "mechanical" fixing methods are known for active and passive implants.

However, none of the previously known approaches concern the fixing of relatively small implants in a target organ which has no fixed (muscular, for example) structures or blood vessels for fixing using a stent or the like. Fixing a drug-eluting implant within a liver tumor, or an RF sensor implant in the lung tissue, for example, is not currently known.

Such implants have not been known heretofore, so that fixing in the above-referenced tissue structures also has not been necessary. However, with advances in RF technology and other technology, such as the packing of medications in magnetic nanostructures, such applications are becoming increasingly important, and the problem of fixing must be solved in the future.

BRIEF SUMMARY OF THE INVENTION

A feature of the one or more embodiments of the invention is to allow, for example, micro- and nanometrically packed drug depots or medications to be reliably, repeatedly, and easily concentrated at an appropriately defined site of action. Use with good reproducibility is of primary importance.

This is achieved according to one or more embodiments of the invention by using an implant having an energy converter which is designed to convert energy, preferably applied in a contactless manner, to heat, the energy converter being situated relative to the rest of the implant in such a way that heat generated from the energy conversion is active at an outer surface of the implant.

Such an implant allows energy to be externally applied in a contactless manner, the energy then being converted to heat by the energy converter. The heat becomes active at at least one outer surface of the implant, and results in tissue coagulation. The tissue coagulation causes blood clotting due to necrosis of the tissue, which in turn results in encapsulation of the implant, and thus, fixing in the target organ.

Accordingly, the energy converter should be designed so that it is able to absorb a sufficiently high power level and correspondingly emit a sufficiently high thermal output in order to cause such tissue coagulation.

To support such encapsulation of the implant, according to one preferred embodiment variant the implant may be coated with an active substance which promotes clotting in order to thus reduce bleeding complications, for example highly vascularized tumors, in the target organ. Accordingly, the coating may contain coagulation factors and in particular vitamin K and/or aprotinin as active substance.

This results in an active or passive implant which may be permanently implanted in the human body and the organs thereof, and which has a surface or a surface coating that causes encapsulation of the implant in the surrounding tissue.

The implant may, for example, be a permanent magnet or be composed of a magnetizable and demagnetizable material in order to concentrate micro- or nanometrically packed drug depots at a desired site of action. These drug depots comprise or contain ferromagnetic carrier structures which are able to absorb a medication and circulate it through the body via the bloodstream. The active substances are released either by a defined elution or by disintegration of the biodegradable carrier structure ($Fe_3O_4$, for example). If the implant is made of a demagnetizable material, within the scope of sequential therapy a site of action for the therapy may be selectively "turned on or off."

Moreover, the implant is preferably composed of a biodegradable material, so that the implant is degraded by the body over time.

In addition, drug depots may be provided at the implant which may contain medications that are released, i.e., eluted, over time after the implantation.

The implant may also be an active implant having a medication pump, or a drug depot which releases in a targeted manner.

Additionally or alternatively, the implant may be an active or passive sensor implant for monitoring one or more physiological parameters. In this case the implant could be an RFID implant, for example, which is known per se.

To achieve the object stated at the outset, a combination of an implant of the type described above with an applicator is proposed which on the one hand is used to insert the implant into the body, and on the other hand preferably allows injection or application of energy into the implant. Such an applicator is used only temporarily for inserting and fixing the implant, and may be removed after the implantation.

Additionally or alternatively, the applicator may also be a biopsy device which allows simultaneous removal of a tissue sample and application of the implant. According to one preferred embodiment variant, the applicator is also designed to apply energy to the implant via the applicator to bring about fixing in the tissue.

According to one variant, the energy converter is designed to absorb electrical power applied via an alternating electromagnetic field. In this case the energy converter contains an electric heating element which converts the absorbed electrical power to thermal power. For absorbing power from an alternating electromagnetic field, the converter preferably has an antenna or is connected to an antenna. The antenna may be part of a resonator which is tuned to a frequency of an alternating electromagnetic field.

Alternatively, the energy converter may have a coil so that electrical power may be applied inductively, i.e., via an essentially magnetic field.

According to a further alternative, the energy converter may also be designed for converting acoustic energy to thermal energy, and for this purpose has a corresponding mechanical resonator which is tuned to the frequency of applied ultrasound energy.

For an implant whose energy converter is designed for absorbing energy via a high-frequency alternating electromagnetic field, the energy converter preferably has an antenna or is connected to an antenna (see above). The antenna may be part of an applicator, for example (also see above), or may be a separate part composed of absorbable materials, for example. In this case the antenna could contain an insulator made of a degradable polymer, and a conductor made of a degradable metal such as magnesium, for example.

The implant is preferably shorter than 10 cm, and therefore is small enough to be MRT-compatible. The antenna which is connected to the implant and to the energy converter thereof may be longer, in particular when the antenna, as stated above, has a bioabsorbable design, so that the implant is once again MRT-compatible after the antenna degrades. As mentioned above, the implant is preferably a very small implant having a mass of less than 10 g, particularly preferably less than 1 g. The volume of the implant is preferably less than 10 cm$^3$ and particularly preferably less than 1 cm$^3$. Even smaller implants having a volume of less than 10 mm$^3$, or even better, less than 1 mm$^3$, are very particularly preferred, and are especially suited as drug carriers for the local administration of medications.

According to one preferred alternative embodiment, the implant is connected to an extraction aid which allows the implant to be removed after the medication has been delivered or monitoring has been completed. Such an extraction aid is not necessary if, as described above, the implant is composed completely of bioabsorbable or biodegradable material.

The implant and its energy converter are preferably designed to carry out hyperthermia treatment, i.e., a treatment based on heating the tissue above the natural body temperature without resulting in coagulation. In this case the implant and the energy converter may advantageously also be used for fixing the implant by means of tissue coagulation by appropriately overheating the tissue, so that after fixing is performed hyperthermia treatment may be carried out using the implant. For the purposes of tissue necrosis by means of coagulation and hyperthermia treatment, however, different energy converters may be provided to allow better adaptation of the respective energy converter to the particular specialized purpose.

BRIEF DESCRIPTION OF THE DRAWINGS

One or more embodiments of the invention is explained in greater detail below with reference to the figures, which show the following:

FIG. 5: shows an implant having an HF antenna.

DETAILED DESCRIPTION OF THE INVENTION

Figure 1:
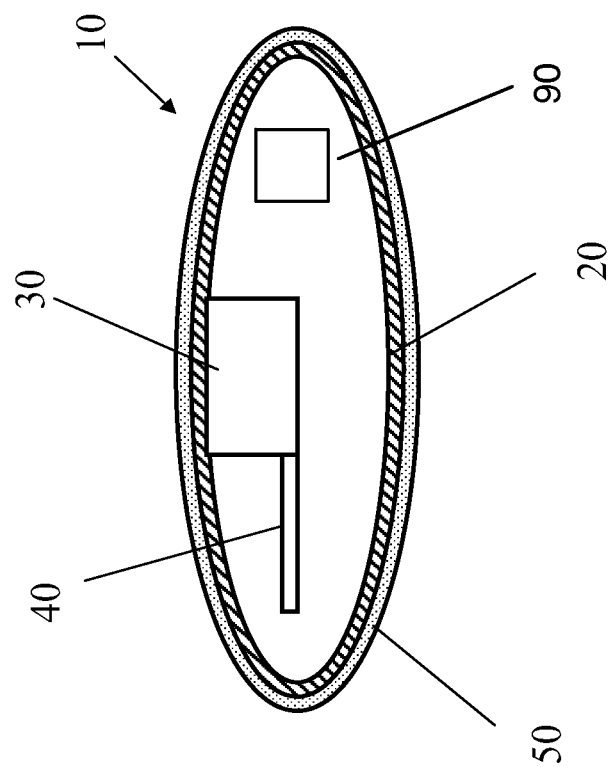
FIG. 1: shows an implant according to the invention in a schematic illustration.

FIG. 1 shows an implant 10 according to the invention, designed as a microimplant having a heat-conducting housing 20, and having an energy converter 30 which has an energy receiver 40 or which is connected thereto. The energy receiver 40 may be a mechanical resonator, an antenna for receiving high-frequency electromagnetic radiation, or a coil for magnetic induction of power. The power received via a high-frequency alternating electromagnetic field by means of an antenna, or the power received via a coil by induction, is thus available as electrical power. In this case the energy converter 30 preferably contains an electric heating element which converts the electrical power to heat. Such an electric heating element could be designed as an ohmic resistor, for example.

The energy receiver 40 is connected to the actual energy converter 30 in such a way that energy received via the energy receiver 40 is converted to heat by the energy converter 30. The energy converter 30 should be connected to the housing 20 of the implant 10 in such a way that the heat resulting from the energy conversion is delivered to surrounding tissue via the housing 20 of the implant 10.

The energy converter 30 and the energy receiver 40 as well as the implant 10 itself are designed in such a way that the implant 10 is able to absorb sufficient power via the energy receiver 40, and the energy converter converts this power to heat which is sufficient to cause tissue coagulation in the immediate vicinity of the implant 10, and thus brings about tissue necrosis which results in encapsulation of the implant 10 and thus fixing of the implant 10.

In the preferred embodiment variant described, the implant 10 shown in FIG. 1 is a medication coating 50.

This medication coating 50 may be a therapeutically active substance, for example for tumor control. Additionally or alternatively, however, the medication coating 50 may also contain a coagulation factor, and in particular vitamin K and/or aprotinin, which promote blood clotting and thus on the one hand inhibit bleeding in tumorous tissue and thus counteract spreading of tumor cells, and on the other hand facilitate fixing of the implant.

In this regard it is noted that fixing the implant by encapsulation due to tissue coagulation also has the advantage that spreading of tumor cells is likewise reduced.

As mentioned above, the implant 10 may also contain selective drug depots 90, or may be designed as an active or passive sensor implant 10, for example as an RFID implant. All components of the implant 10 may be made of biodegradable or bioabsorbable material, and may contain biodegradable metals such as magnesium, for example. Possible sensors for such an implant are sensors for localized pressure measurement, potentiometric pH sensors, or temperature sensors.

As described in further detail with reference to FIG. 3, the implant 10 may also be magnetic, so that ferromagnetic drug depots may be magnetically coupled to the implant 10, or the implant may attract this injected magnetic, nanometrically packed drug depot.

Figure 2:
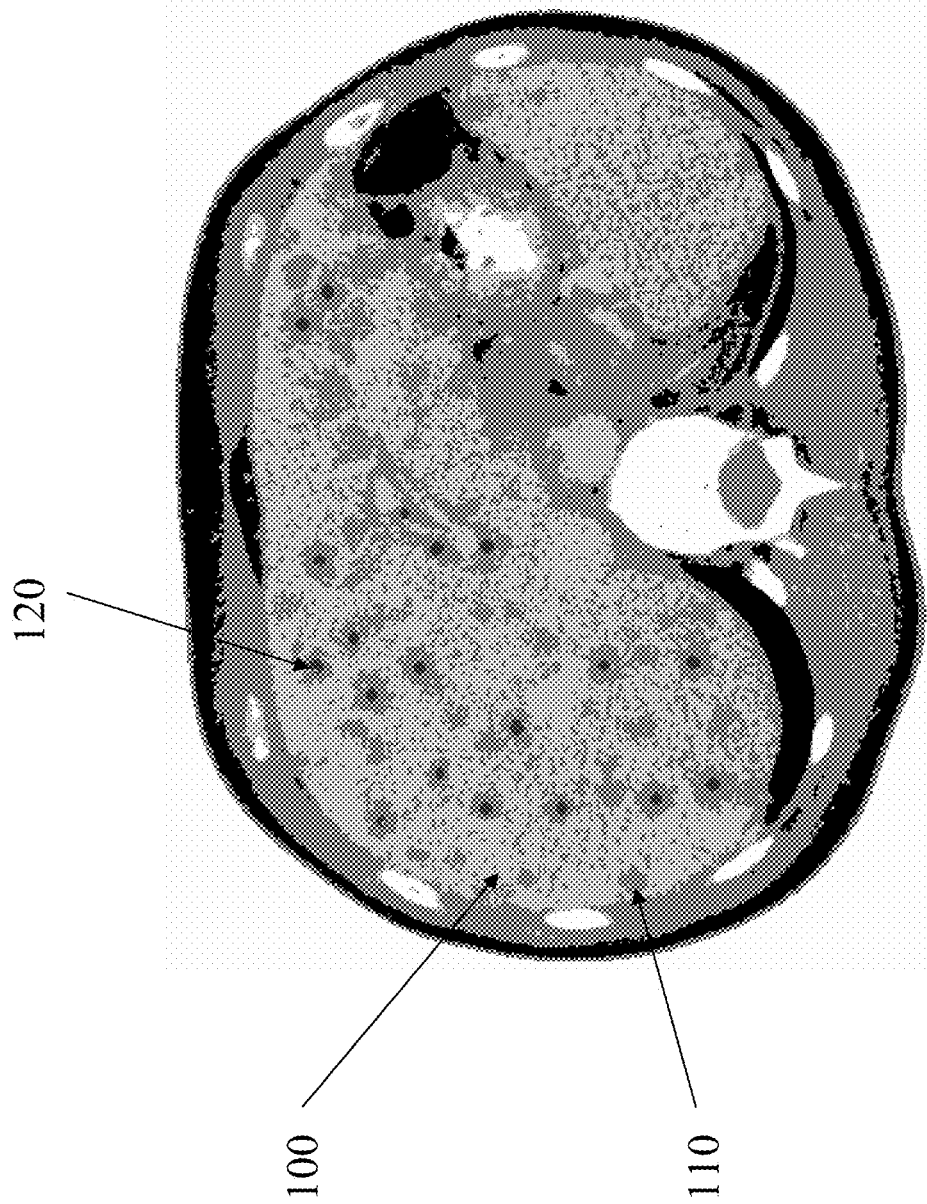
FIG. 2: shows multiple implants in a target organ.

FIG. 2 shows a magnetic resonance tomogram of the liver. In this case the liver 100 is penetrated by multiple metastases 110 which may still be satisfactorily removed from healthy tissue. For concentrating the tumor medication, multiple implants 120 in the form of permanent magnets are implanted in the metastases, using a puncture technique, which concentrate a medication, which is incorporated into ferromagnetic, absorbable nano drug depots and which is effective against tumors, in the target area. After the depots (composed of Fe$_3$O$_4$, for example) have degraded, the intense local action of the normally strong systemic active substances takes effect.

Figure 3:
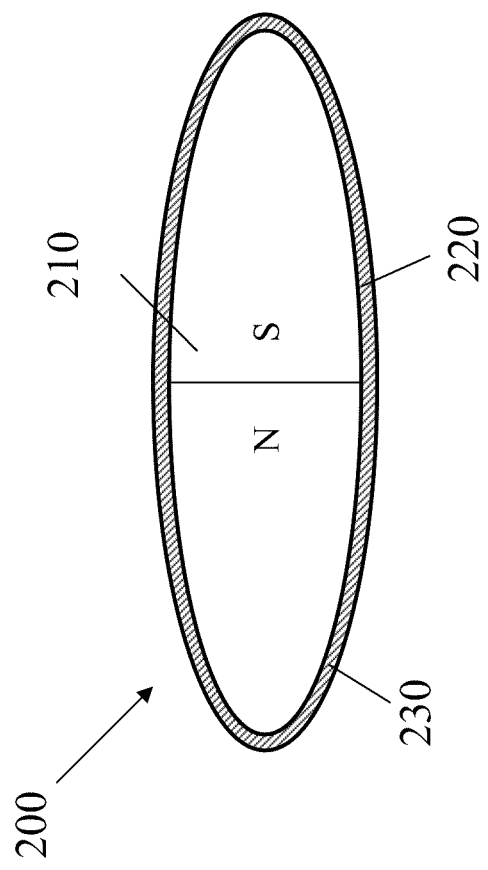
FIG. 3: shows an implantable magnet coated with medication.

FIG. 3 illustrates an implant in the form of an implantable magnet or an implant with the magnetizbale and demagnetizable material 200. In at least one embodiment the implantable magnet 200 may include a permanent magnetic core 210 of which is coated with a coagulation-promoting medication 220 (for example, coagulation factors, vitamin K, or aprotin). This coating in turn is enclosed by a bioabsorbable protective and sliding layer 230, so that the medication containing active substance is delivered only after application into the target organ.

The illustrated implantable magnet is, for example, less than 3 mm in length and less than 1 mm in diameter. The preferred material for the magnet is a neodymium compound coated with a biocompatible material.

The purpose of the medicated coating is to minimize the risk of bleeding for implantation in highly vascularized tumorous tissue, and to form a necrotic capsule around the implant so that fixation of the implantable magnet occurs. The implantable magnet itself is used to concentrate the medication in a therapeutic target area by injecting the medication which is bound to nanometric magnetic carrier substances.

Figure 4:
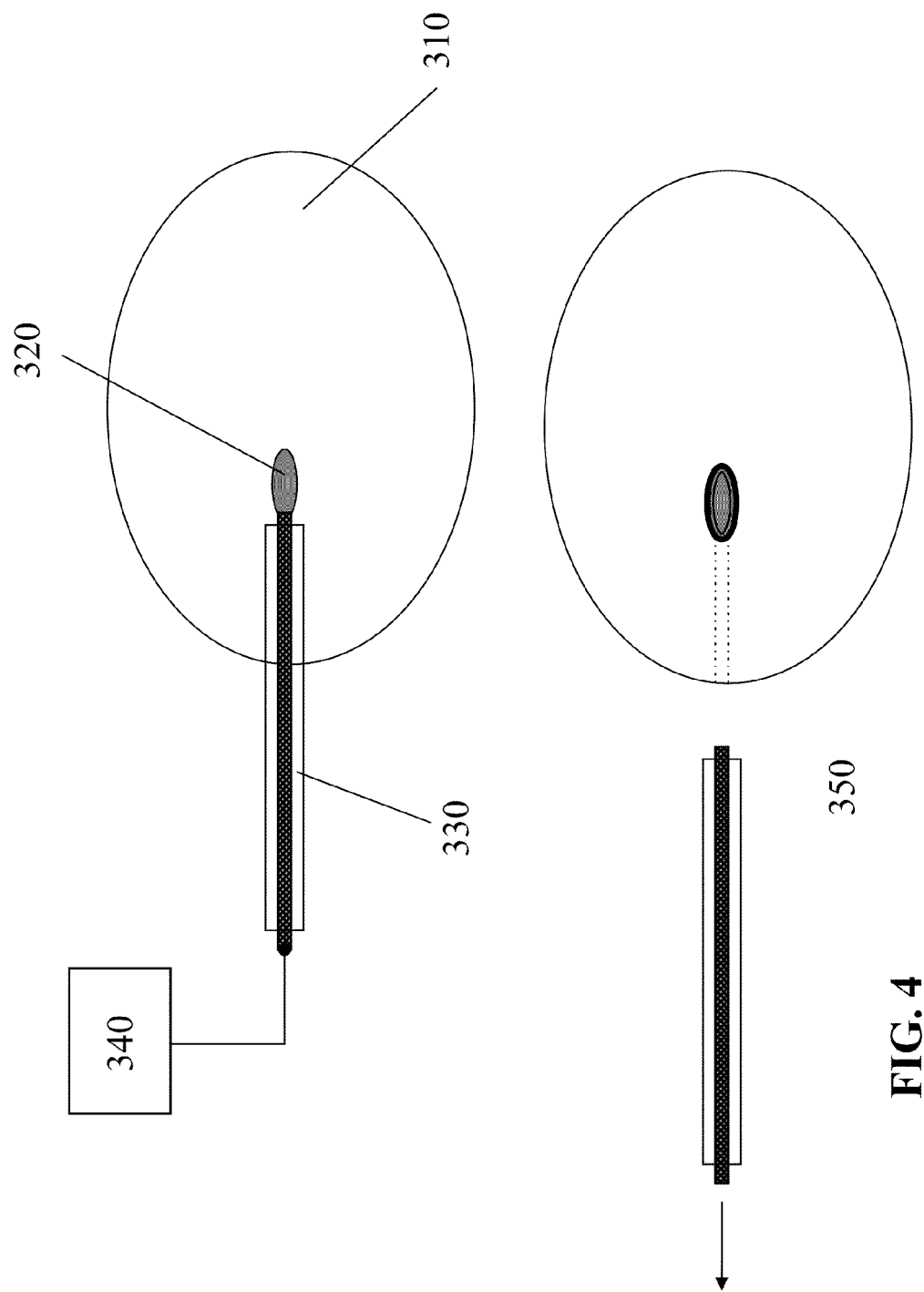
FIG. 4: shows an applicator having an implant for HF coagulation.

FIG. 4 illustrates a target organ 310 in which an implant 320 has been implanted using an applicator 330 in the puncture technique. For fixing the implant, energy is supplied to the implant, using a connected HF generator 340, in such a way that heating of the implant and the surrounding tissue takes place, thus promoting rapid necrosis.

The connection between the applicator and the implant is detachable (by means of a screw connection or the like), thus enabling the applicator to be subsequently removed (see 350).

The applicator is optionally designed in such a way that it functions as a biopsy device. In this design the applicator is composed of an external biopsy needle and replaceable internal applicators. These internal applicators are provided for biopsy in the customary shape of a biopsy device, and are used for tissue removal. After the biopsy, the implant may be positioned at the identical puncture site by use of an applicator, the applicator maintaining electrical contact with the implant so that the HF energy may be applied to the implant. The internal applicator is electrically insulated from the external biopsy needle, thus allowing the latter to act as a counterelectrode for the HF generator.

In an alternative design, energy is applied to the implant using focused ultrasound energy (high-intensity focused ultrasound (HIFU)). In this case the energy converter is designed for converting acoustic energy to thermal energy, and preferably has a resonator which is tuned to the frequency of applied ultrasound energy.

The implant 420 illustrated in FIG. 5 may, for example, be:

an implantable medication pump having an independent power supply, or an implantable medication pump for medication on demand, without an independent power supply, controlled by an external power connection, or an implant for hyperthermia treatment which causes selective heating of tissue via conversion of externally applied energy, whereby an energy converter of an MRT system may preferably be used, and the therapeutic control is achieved using different MRT frequencies or controllable demodulators in the hyperthermia implant, or a sensor implant having an independent power supply and a telemetry function (for example, a glucose or pH sensor), or a sensor implant without an independent power supply and having an external query function (using ultrasound, for example), or an implantable drug depot having a fixed or controllable elution rate.

The following are also illustrated in FIG. 5:
the target organ 410,
an antenna line 430 for applying HF energy, and which may simultaneously be used as an extraction aid, and a flat counterelectrode 440 for HF coagulation, the surface area being much larger than the implant surface so that relevant heating occurs only at the implant.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable device comprising:
an implant comprising:
a housing with an outer surface;
an energy converter connected to said housing and surrounded by said housing,
wherein the energy converter comprises an electric heat converter;
an energy receiver connected to said electric heat converter that receives electrical power,
wherein said electric heat converter is configured to convert said electrical power to heat in a contactless manner to apply said heat to surrounding tissue to fix said implant to said surrounding tissue,
wherein the electric heat converter is situated such that the heat generated from energy conversion by the electric heat converter is active at the outer surface of said housing, and
wherein said electric heat converter is configured to convert said electrical power to said heat such that said heat at said outer surface is delivered to said surrounding tissue via said housing to encapsulate the implant and fix said implant to the surrounding tissue by tissue coagulation by overheating the surrounding tissue, and,
wherein the energy receiver comprises an antenna,
wherein the antenna is configured to receive said electrical power via an alternating electromagnetic field,
wherein said antenna is connected to the electric heat converter such that said electrical power is converted to said heat by the electric heat converter, and,
wherein said antenna is part of a resonator tuned to a frequency of said alternating electromagnetic field;
drug depots configured to release medication, and,
a magnetizable and demagnetizable material magnetically coupled to said drug depots, such that said magnetizable and demagnetizable material concentrates said drug depots at a desired site of action.

2. The implant according to claim 1, wherein the implant comprises a coating with an active substance which promotes clotting.

3. The implantable device according to claim 1, wherein the implant comprises a permanent magnet.

4. The implantable device according to claim 1, wherein the implant comprises a biodegradable material.

5. The implantable device according to claim 1, further comprising an applicator configured to inject high frequency energy that results in said tissue coagulation around the implant, wherein the implant is detachably connected to the applicator.

6. The implantable device according to claim 5, wherein the applicator comprises a biopsy device configured to simultaneously remove a tissue sample and to position the implant.

7. The implantable device according to claim 1, wherein the antenna further comprises absorbable materials.

8. The implantable device according to claim 1, wherein the implant comprises a medication pump.

9. The implantable device according to claim 1, wherein the implant comprises an active or passive sensor implant configured to monitor one or more physiological parameters.

10. The implantable device according to claim 1, wherein the energy converter is further configured to apply a hyperthermia treatment, and
wherein:
the energy converter comprises said electric heat converter that is used to both fix the implant to the surrounding tissue by said tissue coagulation and apply said hyperthermia treatment, or
said implant comprises said electric heat converter that is used to fix the implant to the surrounding tissue by said tissue coagulation and a mechanism different from the electric heat converter that is used to apply said hyperthermia treatment.

11. The implantable device according to claim 10, wherein the mechanism different from the electric heat converter comprises a coating and wherein said coating comprises vitamin K or aprotinin or both that promotes clotting.

12. The implantable device according to claim 1, wherein said drug depots comprise ferromagnetic carrier structures magnetically coupled to said implant that are configured to absorb said medication and to circulate said medication through a body via a bloodstream, such that said medication is bound to said ferromagnetic carrier structures.

13. The implantable device according to claim 1, wherein said antenna is degradable and comprises an insulator comprising a degradable polymer and a conductor comprising degradable metal, such that when said antenna degrades, said implant is magnetic resonance therapy compatible.

* * * * *